US00PP08794P

United States Patent [19]

VandenBerg

[11] Patent Number: Plant 8,794

[45] Date of Patent: Jun. 21, 1994

[54] CHRYSANTHEMUM PLANT NAMED PEACH CANTATA

[75] Inventor: Cornelis P. VandenBerg, Salinas, Calif.

[73] Assignee: Yoder Brothers, Inc., Barberton, Ohio

[21] Appl. No.: 35,958

[22] Filed: Mar. 23, 1993

[51] Int. Cl.[5] ..... A01H 5/00

[52] U.S. Cl. ..... Plt./82.1

[58] Field of Search ..... Plt. 82.1

[56] References Cited

U.S. PATENT DOCUMENTS

PP 8,172 3/1993 VandenBerg ..... Plt./82.4

4,616,099 10/1986 Sparkes ..... 47/58 X

OTHER PUBLICATIONS

Searle, S. A., et al., (1968) "Use of Gamma and X Rays" *Chrysanthemums the Year Round*, Blandford Press, Ltd., London, pp. 27–29.

Broertjes, C., (1966) "Mutation Breeding of Chrysanthemums" *Euphytica* 15, pp. 156–162.

Broertjes, et al., (1980) "A Mutant of a Mutant of a Mutant of a . . . Irradiation of Progresive Radiation Induced Mutants in a Mutation Breeding Programme with Chrysanthemum morifolium" *Euphytica* 29, pp. 525–530.

Chan, A. R., (1966) "Chrysanthemum and Rose Mutations Induced by X Rays" J. Am. Soc. Hort. Sci., 88, pp. 613–620.

Broertjes, C., et al., "Chrysanthemum" *Mutation Breeding Programs in the Improvement of Vegetatively Propagated Crops*, 1978, Elsevier Sci. Pub. Co., N.Y., pp. 162–175.

Dowrick, G. J. (Ed.), (1966) "The Induction of Mutations in Chrysanthemum Using X and Gamma Radiations", *Euphytica* 15, pp. 204–210.

Gosling, S. G. (Ed.), "Sporting and Radiation", *The Chrysanthemum Manual* 1979, National Chrysanthemum Society, London, pp. 329–336.

Sigurbjornsson, B., "Chapter 8, Induced Mutations", *Crop Breeding*, 1983, ASA, CSSA, pp. 153–176.

*Primary Examiner*—James R. Feyrer

*Attorney, Agent, or Firm*—Foley & Lardner

[57] ABSTRACT

A Chrysanthemum plant named Peach Cantata particularly characterized by its flat capitulum form; daisy capitulum type; soft coral-pink ray floret color; diameter across face of capitulum of 76 to 89 mm when fully opened, when grown as a single stem spray cut mum; photographic flowering response to short days when grown in Salinas, Calif., is 48 to 54 days after start of short days; flowering response in Bogota, Colombia is 64 to 67 days; plant height is 61 to 86 cm when grown in Salinas with 3 to 11 long days prior to start of short days; height is 102 to 112 cm when grown in Bogota with 14 to 15 long days prior to start of short days; peduncle length of the first lateral at flowering after removing the apical bud without growth regulator applications is 5 to 15 cm when grown in Salinas, and 13 to 20 cm when grown in Bogota; peduncle length of the fourth lateral at flowering is 8 to 20 cm when grown in Salinas, and 20 to 23 cm when grown in Bogota; and excellent tolerance to low night temperature for bud initiation and flower development.

1 Drawing Sheet

The present invention comprises a new and distinct cultivar of Chrysanthemum, botanically known as *Dendranthema grandiflora*, and referred to by the cultivar name Peach Cantata.

Peach Cantata, identified as 3408 (87-512C07), is a product of a mutation induction program. The new cultivar was discovered and selected by Cornelis P. VandenBerg on Oct. 25, 1990, in a controlled environment in Salinas, Calif., as one flowering plant within a flowering block established as rooted cuttings from stock plants which had been exposed as unrooted cuttings to an X-ray source of 1500 rads in Fort Myers, Fla., on May 17, 1990.

The irradiated parent cultivar was the cultivar identified as Cantata, disclosed in my Plant patent application Ser. No. 07/745,701, now U.S. Plant Pat. No. 8,172. Cantata can be described as a spray cut mum with a flat capitulum form; a daisy capitulum type, a light pink ray floret color in the red group; diameter across face of capitulum of 76 to 89 mm when fully opened; flowering response period of 46 to 54 days after start of short days in Salinas, Calif., and of 59 to 66 days in Bogota, Colombia; plant height of 69 to 97 cm when grown in Salinas with 3 to 11 long days prior to start of short days, and 94 to 107 cm when grown in Bogota with 14 to 15 long days prior to start of short days; and excellent tolerance to low night temperatures for bud initiation and flower development. The foregoing description of Cantata has a somewhat wider range of measurements than the description of Cantata in the pending application noted. This is based on the continued flowering trials for Cantata after preparing and filing the application for Cantata.

The irradiation program resulting in Peach Cantata had as its primary objective the expansion of color ranges of the parent cultivar Cantata. The irradiation program comprised irradiating cuttings of the parent cultivar at irradation levels of 1500, 1750 and 2000 rads. A total of 1,966 cuttings harvested from a total of 225 irradiated plants were planted on Aug. 27, 1990, Aug. 13, 1990 and Aug. 13, 1990, respectively. Of these, 23 initial selections were made, which selections were then revegetated and reflowered. Three consecutive flowerings resulted in discarding 20 of the original 23 selections on Jul. 26, 1991, while 3 codes were retained as PI (Possible Introduction) status. The three retained codes were further tested in Salinas, Calif., and in Bogota, Colombia, ultimately resulting in the decision to introduce all three remaining selections as Peach Cantata, White Cantata and Lemon Cantata. The latter two cultivars are disclosed in pending plant patent applications.

The first act of asexual reproduction of Peach Cantata was accomplished when vegetative cuttings were taken from the original selection in December 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Peach Cantata are firmly fixed and are retained through successive generations of asexual reproduction.

Peach Cantata has now been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia at temperatures as low as 5-10 degrees Celsius.

The following traits have been repeatedly observed and are determined to be basic characteristics of Peach Cantata, which, in combination, distinguish this Chrysanthemum as a new and distinct cultivar:

1. Flat capitulum form.
2. Daisy capitulum type.
3. Soft coral-pink ray floret color.
4. Diameter across face of capitulum of 76 to 89 mm when fully opened, when grown as a single stem spray cut mum.
5. Photoperiodic flowering response to short days when grown in Salinas, Calif., is 48 to 54 days after start of short days. Flowering response in Bogota, Colombia is 64 to 67 days.
6. Plant height is 61 to 86 cm when grown in Salinas with 3 to 11 long days prior to start of short days; height is 102 to 112 cm when grown in Bogota with 14 to 15 long days prior to start of short days.
7. Peduncle length of the first lateral at flowering after removing the apical bud without growth regulator applications is 5 to 15 cm when grown in Salinas, and 13 to 20 cm when grown in Bogota. Peduncle length of the fourth lateral at flowering is 8 to 20 cm when grown in Salinas, and 20 to 23 cm when grown in Bogota.
8. Excellent tolerance to low night temperatures for bud initiation and flower development.

The accompanying photographic drawing is a side view of a single stem cut spray mum of Peach Cantata, with the colors being as nearly true as possible with illustrations of this type.

Of the commercial cultivars known to the inventor, the most similar in comparison to Peach Cantata is the parent cultivar Cantata. All traits of Peach Cantata are similar to those of Cantata, except for the ray floret color. Peach Cantata has a soft coral-pink ray floret color. When grown side by side with Cantata, Peach Cantata has been both slightly shorter and slightly taller in both Salinas and Bogota, but not consistently so.

In the following description color references are made to The Royal Horticultural Society Colour Chart. The color values were determined on plant material grown as a single stem spray cut mum in Salinas, Calif. on Dec. 15, 1992.

Classification:

*Botanical.*—*Dendranthema grandiflora* cv Peach Cantata.

*Commercial.*—Flat daisy cut spray mum.

INFLORESCENCE

A. Capitulum:

*Form.*—Flat.

*Type.*—Daisy.

*Diameter across face.*—76 to 89 mm when fully opened.

B. Corolla of ray florets:

*Color (general tonality from a distance of three meters).*—Soft coral-pink.

*Color (upper surface).*—36C to 36D, closer to 36D.

*Color (under surface).*—36D.

*Shape.*—Straight, oblong, slightly ribbed.

C. Corolla of disc florets:

*Color (mature).*—14A to 14B.

*Color (immature).*—144B.

D. Reproductive organs:

*Androecium.*—Present on disc florets only; moderate pollen.

*Gynoecium.*—Present on both ray and disc florets.

PLANT

A. General appearance:

*Height.*—61 to 86 cm when grown in Salinas with 3 to 11 long days prior to start of short days; height is 102 to 112 cm when grown in Bogota with 14 to 15 long days prior to start of short days.

B. Foliage:

*Color (upper surface).*—147A.

*Color (under surface).*—147B.

I claim:

1. A new and distinct Chrysanthemum plant named Peach Cantata, as described and illustrated.

* * * * *

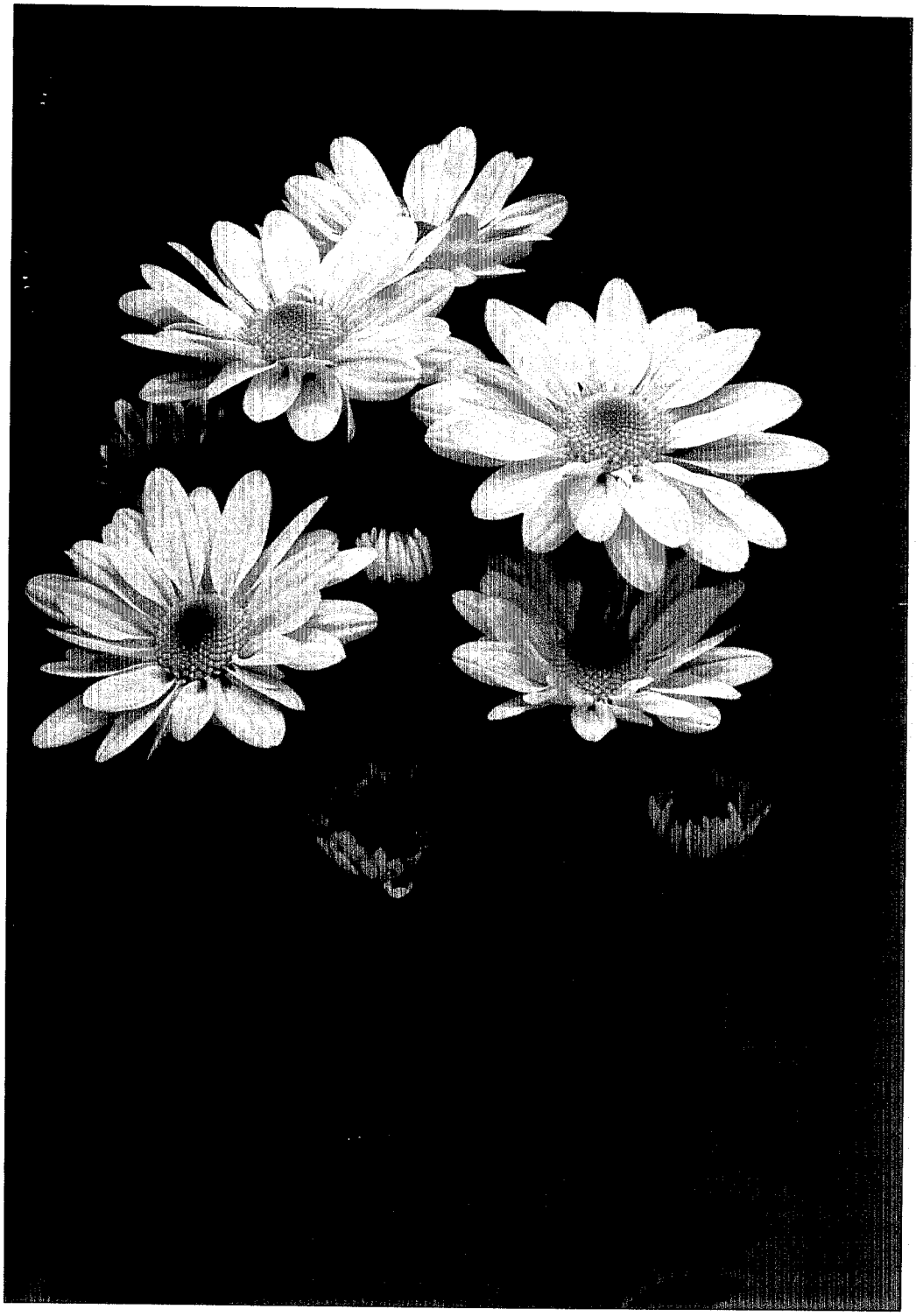

UNITED STATES PATENT AND TRADEMARK OFFICE

CERTIFICATE OF CORRECTION

PATENT NO. : Plant 8,794

DATED : June 21, 1994

INVENTOR(S) : Cornelis P. VANDENBERG

It is certified that error appears in the above-indentified patent and that said Letters Patent is hereby corrected as shown below:

In the Abstract section, line 6, contains a typographical error wherein "photographic" should read --photoperiodic--.

Column 3, line 14, "now" should read --not--.

Signed and Sealed this

Eighteenth Day of October, 1994

*Attest:*

*Attesting Officer*

Bruce Lehman

BRUCE LEHMAN

*Commissioner of Patents and Trademarks*